United States Patent [19]

Schweizer

[11] Patent Number: 4,685,910
[45] Date of Patent: Aug. 11, 1987

[54] APPARATUS AND METHOD FOR DELIVERING SECONDARY FLUIDS TO A PATIENT USING AN INTRAVENOUS ADMINISTRATION SET FEEDING A PRIMARY FLUID

[75] Inventor: Russell J. Schweizer, Crystal Lake, Ill.

[73] Assignee: Abbott Laboratories, North Chicago, Ill.

[21] Appl. No.: 820,852

[22] Filed: Jan. 21, 1986

[51] Int. Cl.$^4$ .............................................. A61M 5/315
[52] U.S. Cl. .................................. 604/218; 604/220; 604/246
[58] Field of Search ............... 604/246, 207, 218, 220, 604/221, 125, 255; 222/378, 389, 394–395

[56] References Cited

U.S. PATENT DOCUMENTS

| | | | |
|---|---|---|---|
| 1,670,605 | 5/1928 | Aeilts | 604/218 |
| 1,853,260 | 4/1932 | Crossett | 604/218 |
| 2,607,344 | 8/1952 | Brown | 604/125 |
| 3,976,068 | 8/1976 | Lundquist | |
| 4,044,758 | 8/1977 | Patel | 604/125 |
| 4,153,186 | 5/1979 | Nye | 604/207 |
| 4,226,236 | 10/1980 | Genese | 604/125 |
| 4,562,844 | 1/1986 | Carpenter et al. | 604/220 |

Primary Examiner—C. Fred Rosenbaum
Assistant Examiner—Gene B. Kartchner
Attorney, Agent, or Firm—Martin L. Katz; Michael J. Roth

[57] ABSTRACT

A device for infusing a secondary fluid through a primary fluid administration set without mixing the primary and secondary fluids is disclosed. Two pistons which are releasably locked in tandem slide within a chamber having an output port, dividing the chamber into two portions. The portion having the outlet port contains the secondary fluid. One piston faces the secondary fluid, while the other has a bore which is in fluid communication with the primary administration set. The pistons can be decoupled, allowing them to move apart to create a third portion in the chamber which can fill with fluid from the primary administration set through the piston which is not in contact with the secondary fluid. When the latter piston is locked in position, a pump in the primary administration set generates pressure in the portion between the pistons. This pressure drives the piston facing the secondary fluid, forcing the secondary fluid out of the chamber and into the patient.

19 Claims, 11 Drawing Figures

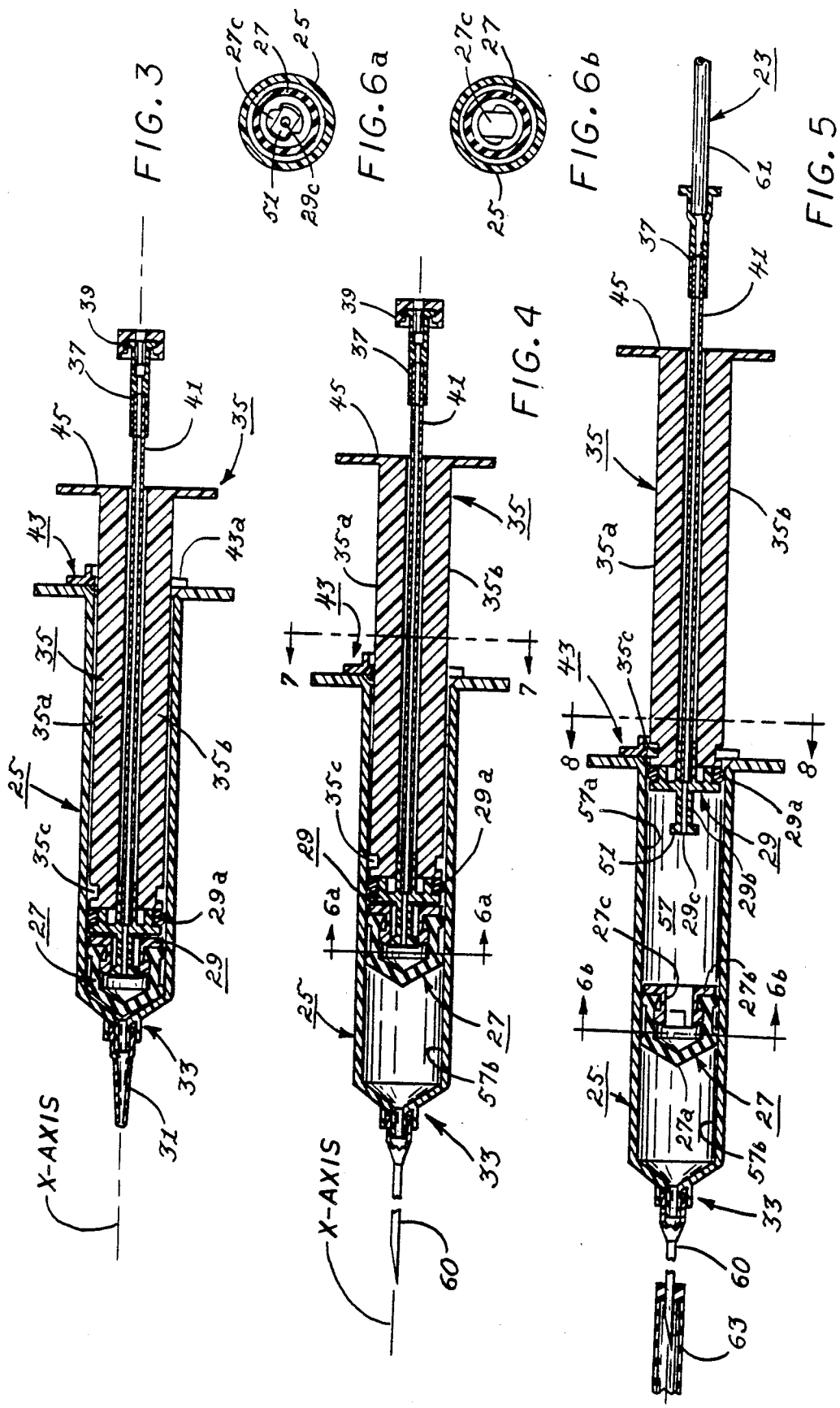

APPARATUS AND METHOD FOR DELIVERING SECONDARY FLUIDS TO A PATIENT USING AN INTRAVENOUS ADMINISTRATION SET FEEDING A PRIMARY FLUID

TECHNICAL FIELD

The invention generally relates to apparatus for delivering supplemental medications to patients by way of administration sets intended for delivery of primary fluids, such as glucose solutions, to patients. More particularly, the invention relates to apparatus for delivering supplemental medications to patients without mixing the medication with the primary fluid of the administration sets.

BACKGROUND

Devices for delivering special fluids (e.g., antibiotics, blood, anesthesia and the like) to a patient by way of conventional administration sets are known. For example, it has long been known to load a simple syringe with a fluid and inject the fluid into the tubing of an administration set delivering primary fluid to a patient. Once in the tubing, the special fluid (hereinafter referred to as secondary fluid) is directed to the patient with the flow of the primary fluid in the set. This approach has the benefit of not requiring a second infusion pump and a second catheter site.

Unfortunately, many secondary fluids are not compatible with the primary fluid of the set and, when mixed, they may form dangerous precipitates. Another undesirable, but less dangerous, characteristic of some combinations of primary and secondary fluids is a tendency for the two fluids to not mix well, resulting in the administration of the secondary fluid at a rate other than the desired rate.

To remedy the problems caused by fluid incompatibilities, devices have been developed which isolate the secondary fluid for transmission to the patient as a bolus, thereby insuring a proper flow rate without necessitating a second pump and catheter site. Unfortunately, these devices are relatively complex and typically not reusable; therefore, they may represent a significant expense to a cost conscious hospital administration.

SUMMARY OF THE INVENTION

It is the primary object of the invention to provide an inexpensive apparatus which can be placed in line with an administration set of primary fluid for delivering to a patient a measured, unmixed volume of secondary fluid. In this connection, it is a related object of this invention to provide an apparatus for unmixed delivery of a secondary fluid which does not require all its component parts to be custom designed.

It is another object of this invention to provide an apparatus for delivering a measured volume of unmixed secondary fluid which meets the foregoing objects yet delivers secondary fluids with satisfactory accuracy of flow rates.

It is a further object of this invention to provide an in-line apparatus for delivering a measured volume of secondary fluid wherein the apparatus can be pre-filled with the fluid. It is a related object to provide an apparatus which can be pre-filled as easily as a conventional syringe is pre-filled.

A more detailed object of the invention is to achieve the foregoing objectives by providing an apparatus which uses a syringe casing as a chamber for placement in line with an administration set in order to deliver a measured volume of secondary fluid into a patient. The conventional sealing piston and plunger of the syringe are replaced by tandem first and second pistons according to the invention. The first and second pistons may be manipulated either in tandem or individually by a plunger constructed in accordance with the invention so as to first cause movement of the pistons in tandem for drawing a secondary fluid into the syringe and sequential second and third movements of the individual first and second pistons which infuse the secondary fluid into the patient at the desired rate.

These and other objects and advantages of the invention will become more apparent from the following detailed description when taken in conjunction with the accompanying drawings.

BRIEF DESCRIPTION OF THE DRAWINGS

FIG. 3 is a longitudinal cross sectional view of the device in FIG. 2, illustrating a plunger and an associated tandem arrangement of sealing pistons according to the invention in a first position before the secondary fluid is drawn into the syringe;

FIG. 4 is the same cross sectional view as illustrated in FIG. 3, except the tandem sealing pistons have been moved to a second position in response to the partial withdrawal of the plunger from the chamber of the syringe, thereby causing a measured volume of secondary fluid to be drawn into the syringe;

FIG. 5 is the same cross sectional view as illustrated in FIGS. 3 and 4, except the tandem sealing pistons have been separated in response to rotation of the plunger so as to allow pressurized primary fluid to enter the upper portion of the syringe and force the piston separating the primary fluid from the secondary fluid to slide toward the bottom of the syringe, thereby infusing the secondary fluid into the patient;

FIG. 6a is a cross sectional view of the device taken along the line 6a—6a in FIG. 4, illustrating in a locked position the male and female portions of a mechanical connector for releasably locking the tandem sealing pistons;

FIG. 6b is a cross sectional view of the device taken along the line 6b—6b in FIG. 5, illustrating the female portion of the mechanical connector with the male portion withdrawn and the two pistons separated;

Figure 1:
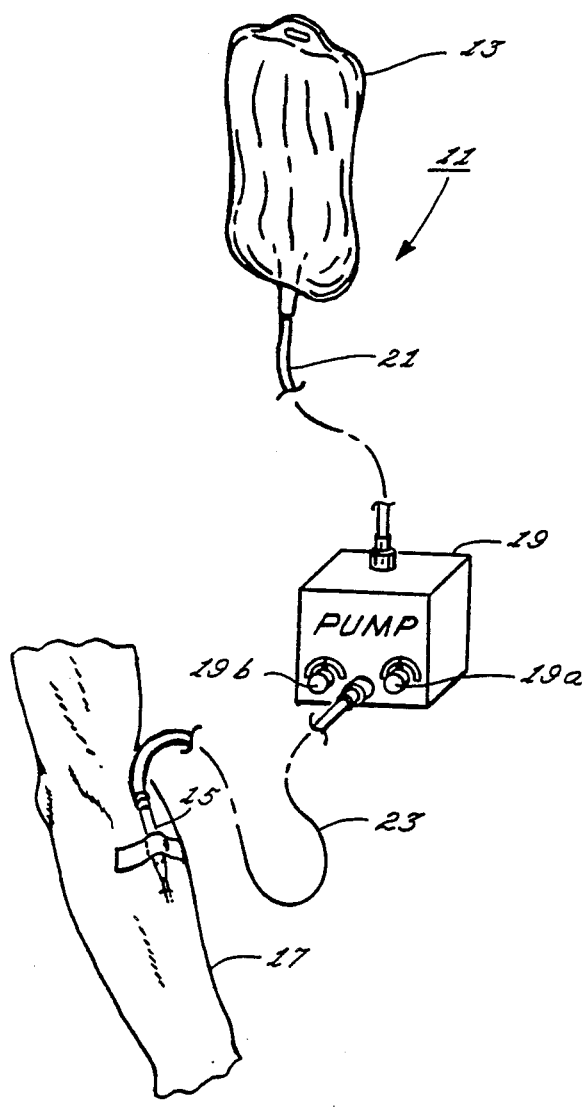
FIG. 1 is a schematic diagram of a conventional administration set and infusion pump for intravenously administrating a primary solution, such as a glucose solution, to a patient.

While the invention is susceptible of various modifications and alternative constructions, the invention is shown in the drawings and herein described in detail with reference to the preferred embodiment, but it is to be understood that the invention is not intended to be limited to the specific form disclosed. On the contrary, it is intended here to cover all modifications and alternative constructions falling within the spirit and scope of the invention as expressed in the appended claims.

DETAILED DESCRIPTION OF THE PREFERRED EMBODIMENT

Turning first to FIG. 1, the invention is practiced in association with a conventional administration set 11 used to intravenously deliver a primary fluid such as a glucose solution to a patient. A reservoir of the primary fluid is typically contained in a receptacle 13 which is fixed at an elevation above the site where a catheter 15 is received by the patient. Typically, the catheter site is in the arm 17 of the patient, but other sites are also commonly used.

In order to provide a precise flow of primary fluid to the patient, a conventional intravenous infusion pump 19 is connected to the downstream end of a first tubing 21 leading from the receptacle 13. A second tubing 23 communicates the pump 19 with the catheter 15, thereby directing the controlled flow of primary fluid from the pump to the patient. As is well known in administration sets using intravenous infusion pumps, the flow rate may be controlled through the adjustment of a flow rate control 19a, and the total volume may be tracked in order to deliver only a predetermined volume as selected by a volume control 19b.

In accordance with one important aspect of the invention, a conventional syringe casing receives first and second slidable sealing pistons secured in tandem in a chamber formed by the syringe casing for first drawing a measured volume of secondary fluid into a first area of the chamber sealed from the ambient air and then separating the pistons to form a second area of the chamber also sealed from the ambient air that receives primary fluid which may be pressurized by the pump 19 so as to enlarge the second area of the chamber and shrink the first area of the chamber, thereby causing the secondary fluid to be metered from the syringe at a rate controlled by the pump. A retainer is snap fitted to the open end of the syringe for (a) preventing the pistons from being withdrawn from the chamber, (b) controlling the mechanical decoupling of the tandem pistons and (c) locking the position of the second piston at the open end of the syringe. A plunger is secured to the second piston, and it extends beyond the open end of the syringe to provide a means for manually moving the pistons in tandem and for decoupling the pistons. When the plunger is pulled to the end of its stroke, the second piston abuts against the retainer. With the plunger fully withdrawn, rotation of the plunger locks the second piston at a position proximate the open end of the syringe so as to provide a rigid assembly. By locking the plunger and the associated second piston in the chamber, accidental movement of the plunger which would cause a sudden and undesirable injection of secondary fluid is prevented.

Referring to FIGS. 2-5, in order to draw a secondary fluid into the conventional syringe 25, a cap 31 is removed from a port 33 at one end of the syringe and a conventional cannula 60 (as shown in FIG. 4) may be attached thereto. Preferably, the port 33 comprises a conventional Luer-type male connector. After a measured volume of a desired secondary fluid has been drawn into the syringe by pulling a pair of pistons 27 and 29 from their seated position at the first end 25a of the syringe shown in FIGS. 2 and 3 to an intermediate position shown in FIG. 4, the port 33 is recapped. The cannula 60 may or may not be removed before the port is recapped, depending on the particular way the syringe is inserted in line with the administration set. The cap 31 may be a vented cap for purposes of sterilization, but the cap placed over the port 33 after the syringe 25 is filled with a drug must not be vented in order to retain the secondary fluid without leakage. To slide the pistons 27 and 29 along the chamber of the syringe casing 25, a plunger 35 is secured to the second piston 29.

After the desired volume of secondary fluid has been drawn into the syringe 25, the device may be stored for later use, or it may be immediately placed in line with the administration set 11. To place the syringe 25 in line with the administration set 11, the tubing 23 connecting the pump 19 to the catheter 15 is broken at a location preferably proximate to the catheter. As illustrated in FIG. 5, the loose end of the tubing 23 is received by a port 37 (preferably a female Luer-type connector) which is normally protected by a cap 39 when unused. Port 37 is the end of a tubing 41 that is fitted into a channel of the plunger 35 and which extends to the second piston 29 where it meets a central bore in the piston.

Figure 7A:
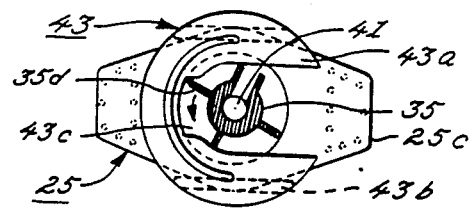
FIG. 7a is a plan view taken along the line 7—7 in FIG. 4, illustrating a retainer according to the invention which snap fits over the open end of the conventional syringe to retain the plunger in the chamber of the syringe, and which limits rotation of the plunger in the chamber between the illustrated locked position and an unlocked position.
Figure 7B:
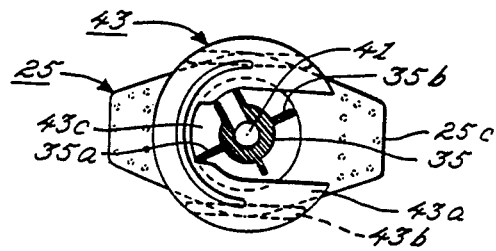
FIG. 7b is the same view as FIG. 7a, except the plunger is rotated to its unlocked position.

In keeping with the invention, means for releasably locking the first and second pistons 27 and 29 together responds to rotation of the plunger 35 either to lock the pistons for sliding movement in tandem (rotation of the plunger in a first direction to the position shown in FIG. 7a) or to unlock the pistons for moving only piston 29 (rotation of the plunger in a second direction to the position shown in FIG. 7b). With a volume of secondary fluid drawn into the syringe 25 and the pistons 27 and 29 intermediately positioned in the chamber of the syringe as shown in FIG. 4, the plunger 35 is rotated from its position in FIG. 7a to the position in FIG. 7b to unlock the pistons 27 and 29.

After tubing 23 has been connected to the port 37 and the tandem pistons 27 and 29 have been unlocked, the pump 19 is turned off so as to allow for gravity feed of the primary fluid, and the plunger 35 is pulled so as to separate the piston 29 from the piston 27, thereby creating a sealed upper and lower subchamber 57a and 57b, respectively within the larger chamber 57 of the syringe 25 as illustrated in FIG. 5. As the plunger 35 continues to move piston 29 away from piston 27, the air pressure in the upper subchamber 57a decreases and thereby creates a pressure differential with the ambient air which pulls the primary fluid from the tubing 23 into the tubing 41 and through the central bore of the piston 29. The primary fluid spills into the upper subchamber 57a from the central bore of the piston 29 and fills the upper subchamber as the piston 29 continues to move toward an open end 25b of the syringe.

At the end of its stroke as illustrated in FIG. 5, the plunger 35 has brought the piston 29 into a locked position proximate the open end 25b of the syringe 25. The syringe 25 is now primed and ready to infuse the desired volume of the secondary fluid into the patient at a controlled rate. With the piston 29 withdrawn from the piston 27 and with the upper subchamber 57a between the pistons filled with primary fluid, the port 33 of the syringe 25 may be either directly connected to the patient's catheter or the cannula 60 may be retained as indicated above and inserted into a conventional reseal 63 at a Y-connector in the line of the administration set as shown in FIG. 5. Preferably, the port 33 of the syringe 25 is connected to the catheter via a conventional extension set (the set should be preprimed). If the rubber reseal 63 and cannula 60 are used, the alternative flow path of the Y-connector must be cut off in order to avoid backflow and/or contamination.

In an alternative embodiment of the invention, a pair of Y-connectors (not shown) are positioned in the tubing of the administration set. The upstream Y-connector is positioned to branch the flow of the primary fluid into a parallel alternative flow paths directed either to the syringe 25 or to a by-pass tubing. The downstream Y-connector re-unites the parallel flow and directs it to the patient. When the syringe 25 is not functioning, it may be isolated from the administration set by clamping the tubing leading to the syringe from the upstream Y-connector and clamping the tubing leading from the syringe to the downstream Y-connector. With such an arrangement, the primary fluid flows only through the by-pass tubing and thereby effectively isolates the syringe from the administration set. To activate the syringe, the previously mentioned upstream and downstream clamps are removed, and a clamp is secured to the by-pass tubing, thereby causing the primary fluid to flow only into the syringe.

After the syringe 25 is connected to the administration set, the pump 19 is activated, and its controls are set to deliver the secondary fluid at a desired rate (control 19a) and to deliver a volume of primary fluid equal to the desired dosage (control 19b) of the secondary fluid held in the syringe. As the pump 19 forces primary fluid into the upper subchamber 57a of the syringe 25 formed by the area between pistons 27 and 29, the fluid pushes against both pistons. Because piston 29 is locked in place as will be explained below, the fluid forces piston 27 to slide toward the end 25a. As the piston 27 continues to slide, it causes the secondary fluid filled in the lower subchamber 57b between the piston 27 and the end 25a of the syringe 25a to be metered out to the patient at the same rate at which the primary fluid is flowing into the upper subchamber 57a.

When the last of the secondary fluid has left the syringe, the piston 27 is seated at the bottom of the syringe 25, and it is abutted against the end 25a. Because the volume of secondary fluid discharged by the syringe 25 approximately equals the volume of primary fluid pumped in the syringe, the volume of primary fluid flow is a sufficiently accurate measure of secondary fluid flow. Therefore, by setting the volume control 19b for the full volume of the secondary fluid contained in the syringe 25, the piston 27 will reach the end 25a of the syringe at approximately the same time the pump automatically turns off. Accordingly, the person administrating the secondary fluid, typically a nurse, need not maintain a constant vigilance of the infusion process. Most conventional pumps 19 include some mechanism for alerting the nurse when the flow of a volume indicated by the setting of control 19b has been achieved.

In order to return the administration set 11 to delivery of primary fluid, the tubing upstream and downstream of the syringe is clamped, and the syringe is removed. The tubing 23 is returned to a direct connection to the catheter 15 and the pump 19 is reset for a desired volume and rate for delivery of the primary fluid.

In keeping with the invention a retainer 43 is press fitted over the open end 25b of the syringe 25 for preventing the plunger 35 and the piston 29 integrally attached to the plunger from being accidentally fully withdrawn from the chamber of the syringe. Referring to the FIGS. 7a and 7b, the retainer 43 includes upper and lower flanges 43a and 43b, respectively, which cooperate to form a channel which receives a rim 25c formed around the open end 25b of the syringe 25. The lower flange 43b is in two sections in order to accommodate wings projecting from the rim 25c which form a biasing surface for the hand of the nurse during the manual movement of the plunger 35 and the associated pistons 27 and 29. A plunger handle 45 performs a similar biasing function in a manner well known in conventional syringes.

The retainer 43 is shaped to allow the plunger 35 free movement along the length of the syringe 25. But, rotation of the plunger about its longitudinal axis is limited by the interaction of a slot 43c in the retainer 43 and a rib 35a of the plunger 35. Rotating the plunger 35 clockwise to its position shown in FIG. 7a locks the pistons 27 and 29 together, thereby providing for movement of the pistons in tandem in response to retraction of the plunger. Rotating plunger 35 counterclockwise to its position shown in FIG. 7b disengages the pistons 27 and 29, and the plunger may pull piston 29 away from piston 27. Pistons 27 and 29 are notched at their periphery as indicated at 47 (FIG. 2) in order to provide for easy visual verification of whether the pistons are locked together.

In order to lock the piston 29 in position when the plunger 35 is fully retracted, each of the ribs 35a and 35b of the plunger is notched at a location 35c such that rotation of the plunger at its fully retracted position will not cause the rib 35a to engage the slot 43c. Thus, the plunger is allowed to continue rotation past its positions shown in FIGS. 7a and 7b and into the position shown in FIG. 8b, thereby causing the ribs 35a and 35b to extend over the upper flange 43a of the retainer 43 and preventing movement of the plunger along its longitudinal axis.

Figure 8A:
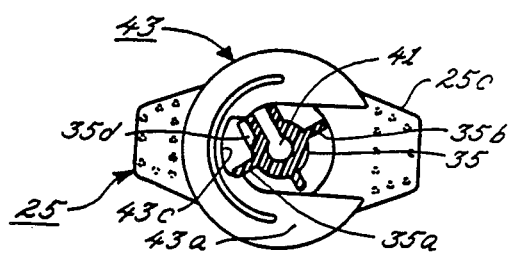
FIG. 8a is a plan view of the retainer taken along the line 8—8 in FIG. 5, illustrating the plunger in a fully withdrawn position.
Figure 8B:
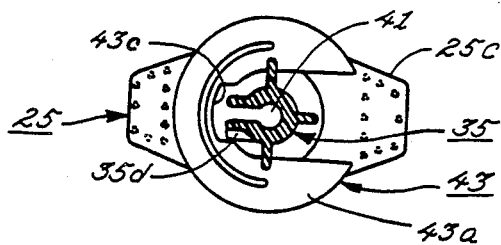
FIG. 8b is the same view as illustrated in FIG. 8a, except the plunger is rotated to a position which causes the retainer to lock the plunger in place and thereby prevent accidental movement of the piston integral with the plunger.
Figure 2:
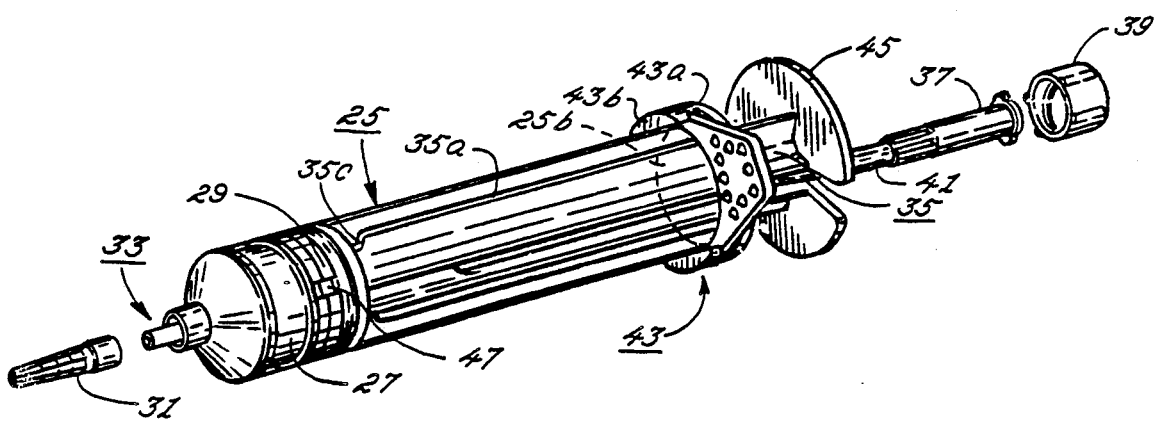
FIG. 2 is a perspective view of a conventional syringe modified in accordance with the invention to provide a device to be placed in line with the administration set of FIG. 1 for delivering a measured volume of a secondary fluid to the patient.

When the plunger 35 is fully retracted as illustrated in FIGS. 8a and 8b, rotation is limited by a stop 35d which is integral with the plunger. The stop 35d extends along the length of the plunger 35 only in an area which is proximate to the retainer 43 when the plunger is fully retracted and, therefore, the stop 35d only interacts with the retainer 43 when the plunger is fully retracted. In the fully retracted position shown in FIGS. 8a and 8b, rotation of the plunger 35 in a counterclockwise direction will bring the ribs 35a and 35b over the top of the retainer 43 and thereby prevent the plunger from moving along its longitudinal axis. As the ribs are rotated to a position over the retainer 43, the stop 35d is rotated to the end of the slot 43c as illustrated in FIG. 8b.

When the plunger 35 is unlocked and retracted, the plunger is positioned as indicated in FIGS. 7b and 8a, and the stop 35d is adjacent the rightmost end of the slot 43c. Therefore, in its retracted position, clockwise rotation of the plunger 35 is prevented, and only counterclockwise rotation can occur. Thus, rotation in only one direction is allowed and, a user can verify by the resistance to further rotation that the plunger is locked in its retracted position. No further confirmation of the locking position is required.

In keeping with the invention, the plunger 35 need not necessarily lock the piston 29 proximate the open end 25b of the syringe, instead the plunger may be modified to lock the piston in positions intermediate this extreme position and the position of the piston 27 after the secondary fluid has been added. For example, the length of the plunger 35 extending beyond the opening 25b of the syringe may be threaded and fitted with a nut so that the piston 27 may be positioned where desired and the nut can thereafter be turned down to the retainer 45, thereby preventing accidental re-insertion of the plunger. By providing such a modified structure, the volume of the upper subchamber 57a can be reduced or minimized, and as a result, the volume of primary fluid lost to the patient is also reduced.

The particular syringe shown in FIGS. 2-5 is a model no. 5663 syringe, manufactured by Becton/Dickinson and Company. Other conventional syringes may also be used in practicing this invention. To the extent other syringes differ in the detail of their shapes, the retainer 43 may be modified to accommodate these differences. But the retainer 43 should remain easily joined to the open end of the syringe (preferably snap fitted) and function to retain the plunger 35 as described. The plunger 35, retainer 43 and pistons 27 and 29 are formed by conventional injection molding processes in conjunction with the well-known techniques of ultrasonic welding and solvent bonding.

In order to releasably lock the pistons 27 and 29 in tandem, the pistons are keyed together by the mating of an axial extension 29b of the second piston 29 with an axial bore 27c of the first piston 27 as shown in FIG. 5. Although the axial extension 29b is generally shaped as a cylinder, the leading edge 51 of the axial extension is preferably shaped as a rectangle when viewed along the longitudinal axis (x-axis in FIGS. 3-5) as shown in FIG. 6a. The axial bore 27c is shaped to have a rectangular cross-section so that the extension 29b can only be inserted into or withdrawn from the bore 27c when the plunger 35 rotates the piston 29 to align the extension and bore.

Preferably, the bore 27c and axial extension 29b are in alignment when the plunger 35 is rotated to the position shown in FIG. 7b. To lock the pistons 27 and 29 together, the rectangular shape of the bore 27c is distorted at the bottom of the bore by notches 65 and 67 (FIG. 6b) which extend the dimensions in the bottom of the bore in order to allow for rotation of the rectangular end 51 of the extension 29b into the notches as shown in FIG. 6a in response to rotation of the plunger to its position shown in FIG. 7a.

With the pistons 27 and 29 locked together, pulling back the plunger 35 works to slide the pistons in tandem along the chamber 57 of the syringe and thereby draw a volume of secondary fluid through the cannula 60 and into the lower subchamber 57b of the syringe 25. The first piston 27 is preferably formed of solid rubber 27a fitted over a plastic core 27b. Piston 29 is integrally formed with the plunger 35 and includes an annular groove which receives a rubber gasket 29a to form a seal between the piston and the inner wall of the syringe.

Rotation of the plunger 35 to its position in FIG. 7b will align the bore 27c and the rectangular end 51, thereby releasing the pistons 27 and 29 so that further pulling of the plunger to the right in FIGS. 3-5 creates the upper subchamber 57a. Before the piston 29 is retracted from the piston 27, the cap 39 is removed and the port 37 receives a male Luer-type connector 61 from the tubing 23.

An axial bore 29c extends through the piston 29 and communicates primary fluid from the tubing 41 to the upper subchamber 57a as the plunger 35 is retracted. After the upper subchamber 57a is filled with primary fluid and the piston 29 is butted against the retainer 43, the plunger 35 is rotated to bring the ribs 35a and 35b over the upper flange 43a of the retainer and thereby lock the piston 29 and plunger 35 in a fully retracted position. By locking the piston 29 and plunger 35 in place, an accidental bumping of the syringe 25 will not cause the piston 29 to move and result in an unwanted and potentially dangerous rapid injection of the secondary fluid 53.

From the foregoing detailed description, it will be appreciated that a conventional syringe casing may be used to easily and inexpensively provide metered infusion of a secondary fluid in line with the flow of primary fluid from an administration set, yet without mixing the primary fluid and secondary fluids. Although a small air pocket remains in the upper subchamber 57a after the upper chamber has filled with primary fluid, applicant has determined any inaccuracy in the measurement of secondary fluid volume flowing to the patient caused by compression of the air bubble is insignificant. Furthermore, the air is isolated from the downstream portion of the administration and, thus, is not a threat to the patient. Therefore, a vent which would increase the complexity and cost of the device is unnecessary. The inexpensive design of the invention using existing syringe casings provides an attractive alternative to more expensive in-line devices for delivering secondary fluids as a bolus to the patient.

I claim:

1. In a fluid administration set for primary fluid whose flow rate is controlled by a pump, a device for infusing secondary fluid through the adminstration set without mixing with the primary and secondary fluids, said device comprising:

a chamber having first and second ends with said first end including an output port;

a sealing piston in said chamber comprising first and second portions;

a plunger integrally secured to said second portion of said sealing piston and extending beyond said second end of said chamber for manually positioning said sealing piston in said chamber between first and second positions wherein the piston is seated proximate to the first end of the chamber in said first position and proximate to the second end of the chamber in said second position;

means responsive to rotation of said plunger about its longitudinal axis for releasably locking said first and second portions of said sealing piston such that retraction of said plunger from said chamber while in a first rotational position causes said first and second portions of said sealing piston to move in tandem away from said first position and thereby draw secondary fluid into said chamber by way of said output port;

said means disengaging said first portion from said second portion in response to rotation of said plunger to a second rotational position such that further retraction of said plunger causes only said second portion to move away from said first end, thereby creating a sealed subchamber between said first and second portions;

means for locking said plunger so as to prevent further movement of said second portion; and a flexible conduit communicating pressurized primary fluid from said administration set to said subchamber to cause primary fluid to fill said subchamber and push said first portion toward said first end of said chamber when said locking means is preventing movement of said second portion, thereby causing the secondary fluid to be directed downstream in the admininstration set and into the patient.

2. A device as set forth in claim 1 wherein said chamber is a conventional syringe having an open end at its second end.

3. A device as set forth in claim 2 wherein said open end of said syringe is capped by a retainer which is press fitted over said open end and which limits rotation of said plunger between said first and second rotational positions.

4. A device as set forth in claim 1 wherein said means comprises a mechanical connector such that said connector is mated in a locked relationship when said plunger is in said first rotational position and mated in an unlocked relationship when said plunger is in said second rotational position.

5. A device as set forth in claim 4 wherein said second end of the chamber is fitted with a retainer for locking said plunger such that said plunger and said second portion of said sealing piston cannot move along the length of said chamber.

6. A device as set forth in claim 5 wherein said plunger includes at least one rib extending along the length of the plunger and projecting into a slot of said retainer such that the interaction of said slot and ribs limit the rotation of said plunger between said first rotational position at one extreme and said second rotational position at the opposite extreme.

7. A device as set forth in claim 6 wherein said rib is notched over a limited distance along its length such that said plunger does not interact with said slot and may continue to rotate past said first or second rotational positions so as to position said ribs to project over the top of said retainer, thereby inhibiting movement of said plunger along the length of said chamber.

8. A device as set forth in claim 7 including a stop integral with said plunger for limiting the free rotation of the plunger otherwise allowed by said notch, said stop limiting rotation of said plunger between a first position which allows free movement of said plunger along the length of said chamber and a second position with said ribs projecting over the top of said retainer thereby preventing movement of said plunger along the length of said chamber.

9. A device as set forth in claim 1 wherein said second portion includes a central bore for communicating said primary fluid from said conduit to said subchamber.

10. A method of infusing into a patient a secondary fluid by using the administration set of primary fluid which includes an in-line chamber having first and second ends and containing first and second sealing pistons in tandem and a conduit communicating an opening in said second piston to an input port, said method comprising the steps of:

slidably moving the pistons in tandem from a first end of said chamber so as to draw secondary fluid into the area of said chamber vacated by said pistons;

decoupling said first and second pistons;

slidably moving said second piston toward the second end of said chamber and drawing primary fluid from an upstream portion of the administration set into the area between said first and second pistons; and directing pressurized primary fluid into the area of said chamber between said first and second pistons, thereby creating a force on said first piston so as to slidably move said first piston toward said first end of the chamber, whereby the movement of said first piston injects secondary fluid into a downstream portion of the administration set.

11. A method as set forth in claim 10 including the step of, locking said second piston in place within said chamber after decoupling said first and second pistons.

12. A method as set forth in claim 10 wherein a retainer is press fitted to a second end of said chamber for locking said second piston into place.

13. In a fluid administration set for delivering primary fluid to a patient and controlling the flow of said primary fluid using a pump, an inline device for infusing secondary fluid without mixing said primary and secondary fluids, said device comprising:

a chamber having first and second ends with an output port at said first end connected to a downstream section of said administration set;

first and second pistons releasably locked in a tandem arrangement for slidable movement between first and second ends of said chamber, said first and second pistons positioned in tandem in said chamber at a predetermined position with secondary fluid filling the volume of the chamber between said pistons and said first end;

first means for sliding said first and second pistons along the length of said chamber and for rotating said second piston between first and second positions;

second means responsive to rotation of said second piston for decoupling said first and second pistons;

third means for communicating primary fluid from an upstream section of said administration set to a centrally located bore in said second piston so as to allow said primary fluid to fill the volume created by the decoupling of said second piston from said first piston; and fourth means for locking said second piston in position within said chamber such that delivery of pressurized primary fluid by said pump into the volume between said decoupled first and second pistons causes said first piston to slidably move toward said first end of said chamber, thereby metering said secondary fluid into the patient.

14. A device as set forth in claim 13 wherein said first means is a plunger integral with said second piston and extending beyond said second end of said chamber so that it may be grasped and pulled or pushed, thereby moving said first and second pistons when locked in tandem or only said second piston when said pistons are unlocked.

15. A device as set forth in claim 13 wherein said second means is a mechanical connector having male and female portions for releasably joining said first and second pistons in response to rotation of said first means.

16. A device as set forth in claim 15 wherein said fourth means is a retainer secured to said second end of said chamber for limiting the ability of said first means to rotate said second piston such that said piston cannot be rotated past its locked or unlocked position.

17. A device as set forth in claim 13 wherein said third means is a conduit associated with said plunger for delivering primary fluid from said upstream section of said administration set to said centrally located bore in said second piston.

18. A device as set forth in claim 14 wherein said fourth means is a retainer secured to the second end of said chamber which interacts with said plunger to lock said second piston at a location along the length of said chamber.

19. A device as set forth in claim 18 wherein said chamber is a conventional syringe housing.

* * * * *